(12) United States Patent
Belbruno

(10) Patent No.: US 10,024,814 B2
(45) Date of Patent: Jul. 17, 2018

(54) MOLECULARLY IMPRINTED POLYMER SENSORS

(71) Applicant: THE TRUSTEES OF DARTMOUTH COLLEGE, Hanover, NH (US)

(72) Inventor: Joseph J. Belbruno, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 100 days.

(21) Appl. No.: 14/954,142

(22) Filed: Nov. 30, 2015

(65) Prior Publication Data
US 2016/0084788 A1 Mar. 24, 2016

Related U.S. Application Data

(63) Continuation of application No. 14/342,059, filed as application No. PCT/US2012/053119 on Aug. 30, 2012, now Pat. No. 9,228,988.

(60) Provisional application No. 61/529,505, filed on Aug. 31, 2011.

(51) Int. Cl.
*G01N 27/22* (2006.01)
*G01N 27/12* (2006.01)
*G01N 33/00* (2006.01)
*B05D 1/00* (2006.01)
*G01N 27/02* (2006.01)

(52) U.S. Cl.
CPC ........... *G01N 27/125* (2013.01); *B05D 1/005* (2013.01); *G01N 27/126* (2013.01); *G01N 33/0047* (2013.01); *G01N 33/0006* (2013.01); *G01N 33/0036* (2013.01); *Y10T 428/2918* (2015.01); *Y10T 436/20* (2015.01); *Y10T 436/200833* (2015.01); *Y10T 436/202499* (2015.01)

(58) Field of Classification Search
CPC ...... G01N 27/227; G01N 27/22; G01N 27/02; G01N 22/00; G01N 3/06; G01N 3/00; G01N 27/12
USPC ........... 422/82.02, 88, 98, 68.1, 50; 436/130
See application file for complete search history.

(56) References Cited

U.S. PATENT DOCUMENTS

| | | | |
|---|---|---|---|
| 5,208,301 A | 5/1993 | Epstein et al. | |
| 5,244,562 A | 9/1993 | Russell | |
| 5,252,292 A | 10/1993 | Hirata et al. | |
| 5,536,473 A | 7/1996 | Monkman et al. | |

(Continued)

FOREIGN PATENT DOCUMENTS

| CN | 101776635 A | 7/2010 |
|---|---|---|
| KR | 100977292 B1 | 8/2010 |

(Continued)

OTHER PUBLICATIONS

U.S. Appl. No. 14/407,860, Office Action dated May 1, 2017.
(Continued)

*Primary Examiner* — Christine T Mui
(74) *Attorney, Agent, or Firm* — Lathrop Gage LLP

(57) ABSTRACT

A molecularly imprinted polymer sensor for sensing a target molecule includes (a) a polymer film that is molecularly imprinted with the target molecule and includes a conductive polymer having resistance sensitive to binding with the target molecule and a structural polymer providing porosity to the polymer film, and (b) interdigitated electrodes, located on a surface of the polymer film, for measuring a change in the resistance to sense said binding.

12 Claims, 12 Drawing Sheets

(56) References Cited

U.S. PATENT DOCUMENTS

| | | | |
|---|---|---|---|
| 5,587,273 A | 12/1996 | Yan et al. | |
| 5,607,573 A | 3/1997 | Miller et al. | |
| 6,046,054 A | 4/2000 | McGeehin et al. | |
| 6,582,971 B1 | 6/2003 | Singh et al. | |
| 6,807,842 B2 | 10/2004 | Williams et al. | |
| 8,615,374 B1 | 12/2013 | Discenzo | |
| 2003/0004426 A1 | 1/2003 | Melker et al. | |
| 2004/0072359 A1 | 4/2004 | Southard | |
| 2004/0126814 A1 | 7/2004 | Singh et al. | |
| 2005/0019218 A1 | 1/2005 | Murray et al. | |
| 2005/0064154 A1* | 3/2005 | Aylward | B41M 3/006 428/195.1 |
| 2005/0126909 A1 | 6/2005 | Weiller et al. | |
| 2006/0079648 A1 | 4/2006 | Lutsen et al. | |
| 2007/0087564 A1 | 4/2007 | Speakman | |
| 2008/0093226 A1 | 4/2008 | Briman et al. | |
| 2008/0150556 A1 | 6/2008 | Han et al. | |
| 2009/0115605 A1 | 5/2009 | Ravenis et al. | |
| 2010/0039124 A1* | 2/2010 | Belbruno | B82Y 15/00 324/693 |
| 2010/0193376 A1 | 8/2010 | Rius et al. | |
| 2010/0214252 A1 | 8/2010 | Wu | |
| 2012/0214252 A1 | 8/2012 | Knop | |
| 2012/0270330 A1 | 10/2012 | Tao et al. | |
| 2012/0285833 A1 | 11/2012 | Liu et al. | |

FOREIGN PATENT DOCUMENTS

| | | |
|---|---|---|
| WO | 2008/007359 A2 | 1/2008 |
| WO | 2008/045596 A2 | 4/2008 |
| WO | 2008/063204 A2 | 5/2008 |
| WO | 2011/136548 A2 | 11/2011 |

OTHER PUBLICATIONS

U.S. Appl. No. 14/407,860, Office Action dated Aug. 16, 2016.
U.S. Appl. No. 13/495,258, Notice of Allowance dated Apr. 22, 2016.
Belbruno et al. (Feb. 2, 2012) "Capacitive sensing of amino acids in molecularly imprinted nylon films," Sensor and Actuators B: Chemical vol. 155(2):915-918.
International Search Report with Written Opinion corresponding to International Patent Application No. PCT/US2011/051169, dated Jan. 30, 2012.
International Search Report with Written Opinion corresponding to International Patent Application No. PCT/US2012/053119, dated Feb. 27, 2013.
International Search Report with Written Opinion corresponding to International Patent Application No. PCT/US2012/053349, dated Feb. 7, 2013.
Liu et al. (2011) "The Development of Chloride Ion Selective Polypyrrole Thin Film on a Layer-by-Layer Carbon Nanotube Working Electrode," Proc. of SPIE. 7983:798315. pp. 1-9.
Sambe et al. (2006) "Uniformly-Sized, Molecularly Imprinted Polymers for Nicotine by Precipitation Polymerization," Journal of Chromatography A. 1134:89-94.
Stozing et al. (2000) "Highly Sensitive Detection and Discrimination of Biogenic Amines Utilizing Arrays of Polyaniline/Carbon Black Composite Vapor Detectors," Chem Mater. 12:593-595.
Thoelen et al. (2008) "A MIP-Based Impedimetric Sensor for the Detection of Low-MW Molecules," Biosensors and Bioelectronics. 23:913-918.
Office Action corresponding to U.S. Appl. No. 13/495,258, dated Dec. 22, 2015.
Office Action corresponding to U.S. Appl. No. 13/495,258, dated Aug. 13, 2015.
Office Action dated Oct. 6, 2017 for U.S. Appl. No. 14/407,860 (11 pages).
Office Action dated Nov. 20, 2017 for U.S. Appl. No. 14/554,634 (13 pages).

* cited by examiner

MOLECULARLY IMPRINTED POLYMER SENSORS

CROSS-REFERENCE TO RELATED APPLICATIONS

The present application is a continuation of U.S. patent application Ser. No. 14/342,059 filed Feb. 28, 2014 and issued as U.S. Pat. No. 9,228,988, which is a National Stage Entry of PCT Patent Application Serial No. PCT/US2012/053119 filed Aug. 30, 2012, which claims the benefit of priority from U.S. Provisional Application Ser. No. 61/529,505 filed Aug. 31, 2011. All of the above mentioned references are incorporated herein in their entireties.

BACKGROUND

Molecular imprinting is a technique that is used to produce molecule specific receptors analogous to biological receptor binding sites. Molecular imprinting of a polymer creates a molecularly imprinted polymer (MIP). An MIP is a polymer that is formed in the presence of a template molecule. The template molecule is removed and leaves a complementary cavity behind in the MIP. The MIP formed demonstrates affinity for the original template molecule.

Sensors for most airborne contaminants are generally active. For example, the sensors require pumps to draw air through a tube. The sensors also require complex analysis after adsorption of the airborne contaminants, and various extracted components must be separated prior to analysis. Furthermore, the sensors are not specific for a single airborne contaminant. The sensors are also not real-time, and only provide an indication of toxic levels in a post-exposure mode. Moreover, some airborne contaminants, such as cyclic volatile methyl siloxanes (cVMS), have been recognized as environmental problems, but there are currently no sensors available for these contaminants.

SUMMARY

This disclosure relates to the field of molecularly imprinted polymers (MIP), and more specifically relates to sensors that include MIP films to detect contaminants. The term contaminants as used herein may mean airborne contaminants, contaminants in a liquid solution, or both.

MIPs disclosed herein may be used for sensors and/or solid phase extraction (SPE). Polymers used to produce the MIPs disclosed herein may be referred to as a polymer host. Molecules disclosed herein for the production of the MIPs may be referred to as a template, a target, or a target molecule.

Embodiments of the sensors provided for herein allow for the detection of even a single kind of airborne contaminant The disclosure provides methods to produce a sensor including a conductive MIP film. The methods involve using the target molecule in the preparation of the MIP films and sensors comprising MIP films. When the target molecule is removed, it leaves behind a MIP with cavities that are complementary in shape and functionality to the target molecule, which can rebind a target identical to the original target molecule in those cavities.

Certain non-limiting embodiments of the MIP sensors provided for herein have conductive elements incorporating thin polyaniline/polyethyleneimine (PANi/PEI) composite films prepared by spin-casting. Certain non-limiting embodiments of the MIP sensors are for formaldehyde detection via changes in conductivity of the MIP. Significant increases in the resistance of these MIP sensor films happen upon exposure to formaldehyde vapor. The films disclosed herein are responsive to other volatile organics, but the response of the films to non-target molecules is significantly reduced. In certain embodiments disclosed herein, detection of a target molecule occurs with changes in the resistance of the MIP. Significant increases in the resistance of the imprinted films occurs when exposed to a target molecule such when compared to control films involving coating with unimprinted polymer. In a non-limiting embodiment, polyvinylpyrrolidinone (PVPy) can be used as a polymer host in a MIP which can then coated onto conductive surfaces such as single-walled carbon nanotubes (SWNT). In general, MIPs can be coated onto carbon nanotubes. In an embodiment, an MIP made from PVPy with cotinine as a target molecule can be coated onto SWNTs. These MIP coated SWNTs can then be applied to a surface such as an electrode to form a sensor for the target molecule.

An embodiment of this disclosure provides for sensors that can be developed to detect a wide range of target molecules using SWNTs coated with MIPs. In one embodiment, reusable SWNT MIP coated sensors created for the detection of cotinine are disclosed.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

In an embodiment, a molecularly imprinted polymer sensor for sensing a target molecule includes a polymer film molecularly imprinted with the target molecule. The polymer film includes (a) a conductive polymer having resistance sensitive to binding with the target molecule, and (b) a structural polymer providing porosity to the polymer film. The molecularly imprinted polymer sensor further includes interdigitated electrodes, located on a surface of the polymer film, for measuring a change in the resistance to sense said binding.

In an embodiment, a method for producing a molecularly imprinted polymer sensor for sensing a target molecule includes depositing interdigitated electrodes on a substrate. The method further includes (a) dissolving a polymer host with a structural polymer and a conductive polymer in a solvent to form a first solution, (b) adding copies of the target molecule to the first solution, and (c) mixing the copies of the target molecule into the first solution to form a molecularly imprinted polymer solution. In addition, the method includes coating the molecularly imprinted polymer solution onto the substrate over the interdigitated electrodes to form a first film and removing the copies of the target molecule from the first film to form a molecularly imprinted polymer film. The molecularly imprinted polymer film has resistance that is (i) sensitive to binding with the target molecule and (ii) measurable using the interdigitated electrodes.

DETAILED DESCRIPTION OF THE EMBODIMENTS

MIP Films and Sensors

Figure 1:
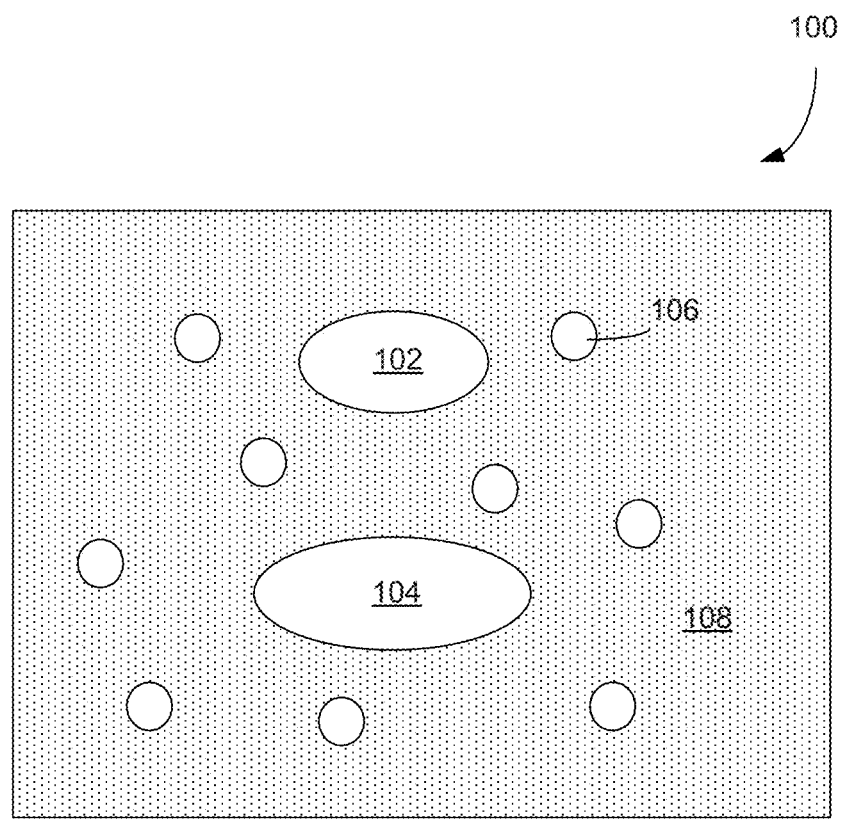
FIG. 1 illustrates a simplified molecularly imprinted polymer solution in an embodiment.

The present disclosure provides methods for producing MIPs. The polymer of a MIP contains binding sites for the target molecule. Without being bound by theory, the target molecule binds to the binding sites in the polymer layer via physical or chemical forces such as electrostatic interactions, Van der Waals forces, ionic bonds or even covalent bonds. The polymer layer of the MIP may also be referred to as the polymer host. The polymer layer (polymer host) of the MIP may contain a structural polymer component (structural component) and a conductive polymer component (conductive component). The structural component of the polymer layer provides the structural support for the polymer layer of the MIP. In an embodiment, the structural component primarily forms the binding site of the polymer host. In an embodiment, the conductive component of the polymer host is a conductor of electrons and allows for the flow of an electrical current through the polymer host.

In an embodiment, the physical property associated with the presence of a target molecule in a MIP film is a change in the resistance of the MIP film with or without the target molecule bound. As used herein, a film generally refers to a coating of a surface. An embodiment of a film is coating of a surface by a polymer or MIP. In one embodiment a MIP film is from about 1 Å to about 10,000 Å. In general, MIP film sensor functionality depends upon detecting differences in the resistivity of the MIP film as a function of the adsorption of a target molecule. In an embodiment, MIP film sensors can be tested for their ability to detect airborne contaminants by using various vapor chambers or otherwise exposing the MIP film sensors disclosed herein to a sample of gas.

In an embodiment, the resistance, R, of the MIP films is measured with a multimeter when a constant current is being applied using two contacts to the MIP films and/or sensors.

The conductive polymer component of the polymer host provides a conductive path for the flow of current within the polymer host. In an embodiment, the polymer host consists of only a conductive component, or only a structural component. In another embodiment, the polymer host consists of any percent composition of both the structural component and the conductive component.

MIP conductive polymers include, but are not limited to, polyaniline (PANi). MIP structural polymers include, but are not limited to poly(4-vinylphenol), polyurethane, nylons, poly(2-vinylpyrole), poly(4-vinylpyridine), polyvinylpyrrolidinone (PVPy), polyethyleneimine (PEI), nylon-6 and polystyrene. Depending upon the MIP polymer of choice, the solvents in which the MIPs have high solubility can include, but are not limited to, alcohols, dimethylformamide, water, formic acid and chloroform. It will be appreciated by those skilled in the art that modification of polymers and/or solvents allow for tuning the process of producing MIPs to the chemistry of a target molecule.

In this disclosure, target molecules include airborne contaminants that are volatile organic solvents. Examples of target molecules include formaldehyde, which is an airborne contaminant from cigarette smoke and many materials in the construction trade; cotinine, which is an airborne contaminant from cigarette smoke; glutaraldehyde, which is used as a disinfectant in medical labs; benzopyrene, which is a polyaromatic hydrocarbon from combustion; toluene and xylene, which are used in many products including paints, adhesives, etc; vinyl chloride and styrene, which are monomers used in production of plastics; chemical warfare agents, such as mustards, nerve gases and phosgene; and cVMS, which are contaminants from personal care products.

In some embodiments of the MIPs disclosed herein, homologous molecules, homologs, of the target molecule can be used instead of the target molecule to produce MIPs that detect the target molecule. Homologs of target molecules include molecules that are similar to the target molecule in various attributes including but not limited to size, electrostatic potentials, electronegativity, charge density, chemical bonding potential, and molecules that have similar shapes to the target molecule. Homologs include isomers and stereoisomers of the target molecule.

Conductive polymers such as PANi are of interest as components of electrochemical devices and as active materials for a variety of sensing applications. In sensors, the key feature of doped, electrically conductive PANi is the presence of protonated nitrogen atoms that give up the proton to an adsorbed vapor molecule, decreasing the conductance of the polymer. Thin films optimize the density and availability of protonated receptor sites and minimize the diffusion distance necessary for the adsorbant to travel during binding events. Thin films also increase the responsivity if the reporting electrode lies beneath the polymer film.

In an embodiment, MIP films can be regenerated by extracting and/or evaporating target molecules from a MIP film by soaking or washing in a solvent in which the polymer host is insoluble, but the target molecule is soluble. In an embodiment, the target molecules can be removed from the MIP binding sites through extraction and/or evaporation processes. The MIP films are then washed and dried to allow the solvent and the target molecule to be separated from the MIP films. After extraction and/or evaporation of the target molecule, the MIP films are ready to detect target molecule again.

Sensing using conductive polymer films can be performed either by coating the surface of an electrode with the doped polymer, a MIP containing bound target molecule, and measuring the cell potential with reference to a redox electrode, or by making a true planar, chemiresistive structure. The latter can be used with a variety of conductive polymers or composites, and may be designed to create higher values of resistance (signal). They have the potential for rapid detection. These planar structures may be designed with good time response by an appropriate choice of geometry and materials. In some embodiments provided herein, a spin casting method for preparing thin films on lithographically produced electrodes and these films have been characterized and shown to be sensitive to target molecules in the vapor phase, also known as a gas phase or gas.

Conductivity measurements of embodiments of the sensors presented herein are indicative of the binding of template molecules. Data are reported as normalized resistance (or the change in resistance), referenced to an initial or background value. The change in the resistance value, and the rate of change in the resistance (the slope), are proportional to the quantity and identity of the molecule adsorbed. Either of the values may be used to quantify and/or detect the target molecule. Additional evidence of target molecules being bound in the MIP layer can be obtained through IR spectroscopy and gas chromatographic experiments.

The morphology of MIP films disclosed herein can be further characterized by scanning electron microscopy.

MIP Coated Carbon Nanotube Films

Single-wall carbon nanotubes (SWCNTs), more generally referred to as carbon nanotubes, exhibit a range of electrical properties depending upon the geometry or chirality of the tube. SWCNTs contain a mixture of metallic and semiconducting material and, when deposited across a pair of electrodes, provide a conductive pathway. Carbon nanotubes may be coated with the insulating polymer PVPy and cast into a film, however this technique has not previously been used for molecularly imprinted polymers, MIPs.

Without being bound by theory, the mechanism for the variation in the resistance of a MIP coated carbon nanotube sensor film relies on the chemical nature of the adsorbant MIP layer and its effect on the nanotube electron energy levels. In an embodiment, the target molecule is a nucleophile, that is, it is relatively electron rich and the MIP structural polymer is non-conductive. The polymer coating of the carbon nanotubes decreases the conductivity of the carbon nanotubes as measured across the electrodes because the MIP coated, conductive nanotubes will not be capable of good electrical contact to the metallic electrode. However, in an embodiment, the imprinted polymer contains an electron rich target molecule that, at the imprint sites, has the ability to add charge to the electrical environment, and thus increasing the conductivity or lowering the resistance of the MIP coated carbon nanotube film.

Carbon nanotubes can be coated with MIPs. In one embodiment, the carbon nanotubes act as a conductor to an electrical current and the MIP coating the carbon nanotube affects the conductivity of the carbon nanotubes according to whether or not a target molecule is bound within the MIP layer. In one embodiment, the MIPs coating the carbon nanotubes can have polymer hosts made from only structural components, for example PYPy. In another embodiment, the MIPs coating the carbon nanotubes can have polymer hosts made from a mixture of both conductive components and structural components. In yet another embodiment, the MIPs coating the carbon nanotubes can have polymer hosts made only conductive components.

In various embodiments, coating methods are provided for coating polymers onto carbon nanotubes. Different coating methods are modified to provide various and different MIP host polymers. In one embodiment, cotinine is used as the target molecule since the carbonyl group on the cotinine interacts with the hydrogen atom in the β-position with respect to the carbonyl group in PVPy to create a chemically based recognition site in the MIP. Because PVPy is a non-conductive polymer, the MIP-based conductive sensor provides evidence that other non-conductive polymers may be used to create new sensors and MIP films based on chemical interactions rather than only on intrinsic polymer conductivity provided by conductive polymer components.

Methods of Making MIP Films and Sensors

The present disclosure provides methods for making MIPs and sensors that use MIPs. In an embodiment, MIPs are made by mixing together a structural component, a conductive component, a target molecule and a first solvent. In an embodiment, a structural component is a structural polymer. In an embodiment, a conductive component is a conductive polymer. In an embodiment, the solution of the polymer components, the first solvent, and the target molecule is a molecularly imprinted polymer solution. The molecularly imprinted polymer solution can then be coated onto a surface such as an electrode and allowed to dry. When the molecularly imprinted polymer solution is drying, the polymers form the binding sites for the dissolved target molecules as the polymer layer polymerizes around the target molecules. Next, the target molecule is selectively removed from the MIP layer by either evaporation of the target molecule or through extraction with a solvent that selectively dissolves the target molecule, but does not dissolve the polymer host.

The solvent used in making the MIPs can boil at a lower temperature than the target molecule. This allows the template to form recognition sites during spin or dip coating. An organic solvent can then be used to remove the template. The organic solvent should be incompatible with the polymer host to promote precipitation of the MIP. Alternatively, the volatile organic molecule or template can be evaporated from the MIP if the solvent has a lower boiling point than the target.

Certain non-limiting embodiments of the MIP sensors provided for herein have polymer hosts containing polyaniline conductive components incorporated into polyethyleneimine structural components as thin PANi/PEI composite films prepared by spin-casting for formaldehyde detection via changes in conductivity. The sensors have significant increases in the resistance of the MIP films upon exposure to formaldehyde vapor in a laboratory chamber. The films are responsive to other volatile organic vapors, but at significantly reduced levels. The morphology of various embodiments of the MIP films have a porous surface well-suited to vapor phase adsorption.

There are various techniques for depositing films including electropolymerization, spin casting and laser deposition. In certain embodiments of the present disclosure, PANi is employed to directly measure the target concentration in concert with a second polymer included in composite materials to improve the porosity of the film.

In an embodiment, MIP films are spin-cast composites of PANi and PEI. PANi in its conductive form is insoluble, but the emeraldine base may be dissolved in several solvents in which PEI is also soluble. In an embodiment, the spin casting solution can be produced as a 5 percent (by weight) solution in each of the two polymers, structural component and conductive component.

In an embodiment, a PANi/PEI polymer layer can be spin-coated onto an electrode. An aliquot of molecularly imprinted polymer solution is dropped onto the electrodes and allowed to spread. The spin-coater device spins the electrode at a given rpm for an amount of time resulting in the deposition of films. In an embodiment, the thickness of the MIP films is about 300 nm.

In an embodiment MIP film sensors are constructed on oxidized silicon substrates with a PANi/PEI composite film as the active element above the electrode. In one non-limiting embodiment, prime grade silicon wafers with a thermally deposited oxide layer are used for the substrate. These oxide layers can be patterned by photolithography and subsequently wet etched to produce electrodes, which are then subjected to a vapor deposition of chromium or other metals and an overlayer of nickel or other like metals. Lift off can be accomplished using acetone, with final rinses of water to produce an electrode patterned into an interdigitated grid.

Methods for Making MIP Coated Carbon Nanotube Films

In an embodiment, MIP coated carbon nanotubes can be prepared by suspending carbon nanotubes, PVPy or other polymers, and target molecules in a first solvent. The first solvent is then sonicated for a period of time. After sonication, the suspension is filtered and washed with the first solvent in order to remove any unbound polymer or target molecules. The dried, MIP coated carbon nanotubes are then re-suspended in the first solvent by sonication.

In another embodiment, the MIP contains only a structural component and a target molecule which are then coated onto carbon nanotubes. The MIP coated carbon nanotubes are then suspended into a solution which is coated onto a surface and allowed to dry. In an embodiment, the surface coated is an electrode. In another embodiment, the surface coated is a semiconductor. In yet another embodiment, the surface coated is an insulator. In an embodiment, the target molecule in the MIP coated carbon nanotube film may be removed by either evaporation or through extraction with a solvent that selectively dissolves the target molecule and not the carbon nanotube or polymer host.

Embodiments of MIP Films and Sensors

FIG. 1 illustrates an embodiment of a simplified molecularly imprinted polymer solution. Molecularly imprinted polymer solution 100 includes a chemical component 102 dissolved in a solvent 108 and a structural component 104 also dissolved in the solvent 108. Polymer solution 100 also includes target molecule 106 dissolved in solvent 108. As illustrated in FIG. 1, target molecule 106 is bonded to the chemical component 102 in the polymer solution 100, also referred to a MIP solution.

Figure 2:
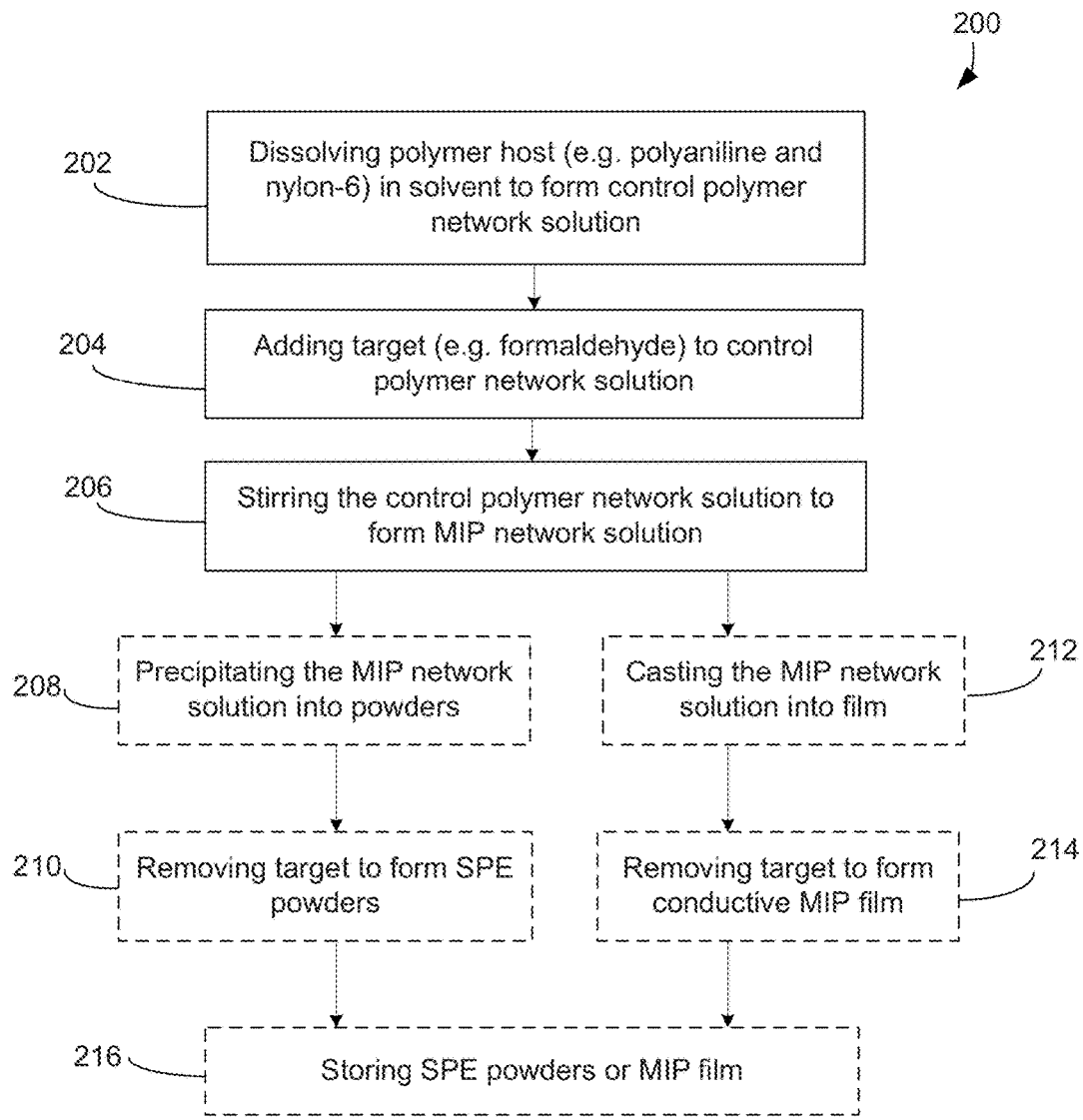
FIG. 2 is a flow chart illustrating the steps of a modified phase inversion process for producing MIPs, in an embodiment.

In an embodiment, conductive MIPs are produced by a modified phase inversion process, as illustrated in FIG. 2. A polymer host generally includes a conductive component and a structural component for a target molecule that is present during the formation of the molecularly imprinted polymer (MIP). For example, polyaniline is a conductive polymer of the host, and nylon-6, polyethyleneimine, or polyvinylpyrrolidinone may be a structural component of the polymer host when these two polymers are used simultaneously. In an embodiment, the polymer host is a conductive polymer. In one embodiment, the polymer host is a structural polymer. In another embodiment, the MIP contains only a structural component such as polyvinylpyrrolidinone and is cast or otherwise coated upon a conductive component or surface such as carbon nanotubes. In an embodiment, the polymer host is only a conductive polymer.

In an embodiment, a process for making MIP films of the present disclosure 200, also referred to as a modified phase inversion process 200, includes dissolving the polymer(s), e.g., polyaniline and nylon-6, of the polymer host sequentially in a suitable solvent to form a first solution at step 202. After dissolution of the polymer host in the solvent, the target molecule (e.g., formaldehyde) or a molecule with similar size and chemical properties as the target molecule (e.g., formic acid and formaldehyde) is added to the first solution at step 204. In an embodiment, the process 200 also includes stirring the first solution to insert or otherwise incorporate the target molecule into the polymer host to form an MIP polymer solution at step 206.

In an embodiment, process 200 further includes precipitating the MIP solution into powders at step 208 and removing the target molecule by addition of a solvent. A suitable solvent for removal or extraction of the target molecule from the MIP is one in which the polymer host is poorly soluble in, but one in which the target molecule is soluble to very soluble in. Using the selective solubility of the target molecule over the polymer host allows for the MIP film to act as a SPE because the target molecule may be selectively bound and then extracted from the polymer host. In an embodiment, the process form making the MIP films disclosed herein can be used to produce SPE powders at step 210. After drying, the SPE powders are ready for use in a solid phase extraction (SPE) tube. In an embodiment, process 200 further includes storing the SPE powders or MIP film at step 216.

In another embodiment, process 200 includes casting the MIP solution into a film at step 212. The MIP film may or may not contain the target molecule. In one embodiment, the cast MIP film does not contain the target molecule at step 214. The MIP film can be used as a membrane or as a sensor and can be formed via any number of techniques, such as spin coating, drop casting, ink jet printing or dip coating, among others. A spin coating procedure for an MIP film is described in the US patent publication US 2010/0039124 A1, entitled "Molecularly Imprinted Polymer Sensor Systems And Related Methods," filed on Jun. 14, 2007, which is incorporated herein by reference. After drying, the MIP film is ready for use in a film based sensor. In an embodiment, process 200 produces a thin film MIP that can serve as part of a sensing device to detect airborne contaminants.

The interaction between a polymer host and a target molecule in a MIP can involve non-covalent bonding, such as hydrogen bonding, between the polymer host and the target molecule. The binding interaction can exploit other electrostatic forces in conjunction with shape recognition, but the interaction between polymer host and the target molecule is not limited to non-covalent forces and can also include ionic and/or covalent chemical bonds between the target molecule and the polymer host.

When the target molecule is removed via extraction or evaporation or by other removal means, it leaves behind a MIP with cavities that are complementary in shape to the target molecule and act as a binding site to the target molecule or similar molecules. The MIP films disclosed herein are capable of rebinding target molecules through subsequent rounds of use when the MIP is regenerated between measurements by removing the target molecule from the MIP before the next use of the MIP film and/or sensor.

In another embodiment, MIPs can be produced by dissolving the polymer or polymer host components, i.e., conductive and structural, and target molecules in a first solvent to form a molecularly imprinted polymer solution. In one embodiment, the target molecule foul's between about 1 and about 30 weight percent of the molecularly imprinted polymer solution. In a preferred embodiment, the target molecule Rums between about 2 and about 20 weight percent of the molecularly imprinted polymer solution. In a more preferred embodiment, the target molecule forms between about 2 and about 15 weight percent of the molecularly imprinted polymer solution.

In an embodiment of a MIP of the present disclosure, the molecularly imprinted polymer solution has a molar ratio of from about 10:1 to about 1:1 to about 1:10 of the structural component to the conductive component. In an embodiment, the molecularly imprinted polymer solution is from about 1 to about 30 percent of the target molecule or homolog by weight. In a preferred embodiment of a MIP of the present disclosure, the molecularly imprinted polymer solution has a molar ratio of from about 5:1 to about 1:1 to about 1:5 of the structural component to the conductive component. In a preferred embodiment, the molecularly imprinted polymer solution is from about 2 to about 20 percent of the target molecule or homolog by weight. In a more preferred embodiment of a MIP of the present disclosure, the molecularly imprinted polymer solution has a molar ratio of from about 1:1 of the structural component to the conductive component. In a more preferred embodiment, the molecularly imprinted polymer solution is from about 2.5 to about 10 percent of the target molecule or homolog by weight.

In an embodiment of a MIP of the present disclosure, nylon-6 is used as the structural component and polyaniline is used as the conductive component for the polymer host of a MIP film having formaldehyde as the target molecule. Formic acid can be used as a homolog for formaldehyde in the production of a MIP film useful for the detection of formaldehyde as the target molecule. Formic acid can be used as both a solvent for dissolving the structural and conductive components as well as a homolog for the target molecule formaldehyde.

The first solvent should be suitable for each component of the polymer host and the target molecule. For example, polyaniline, nylon and formaldehyde are soluble in formic acid. The polymer hosts and solvents can vary for a particular target molecule of interest. Non-limiting examples of solvents can include alcohols, dimethylformamide, water, formic acid and chloroform.

In an embodiment, after dissolving the polymer host components, 2 to 10 weight percent of the target molecule is added in the polymer solution, followed by stirring for about 20 hours to uniformly mix the target in the polymer solution and form the molecularly imprinted polymer solution. In general, when a higher target concentration is used, the sensitivity of the MIP to target detection increases. However, the MIP's detection or separation for a particular molecule or molecular specificity is reduced.

In an embodiment, thin films are produced by spin casting onto glass substrates at a spin rate of about 4000 rpm for a period of about 30 seconds and allowed to air dry for about 1 hour. The final film can be stored until needed for use to rebind the target.

The MIP films produced in process 200 are suitable for use as a sensor that reports the presence of the target molecule via, for example, a color change, either through a polymer incorporated chromaphore or an externally added reagent. Such a film can be built into a capacitor to monitor dielectric changes due to the presence/absence of the target molecule. Alternatively, if the polymer is conductive, a resistor that monitors the presence of the target molecule via conductivity changes can be constructed. Conductivity can be incorporated into the MIP by using a conductive polymer such as polyaniline and a structural polymer component that provides the actual recognition sites.

Figure 3A:
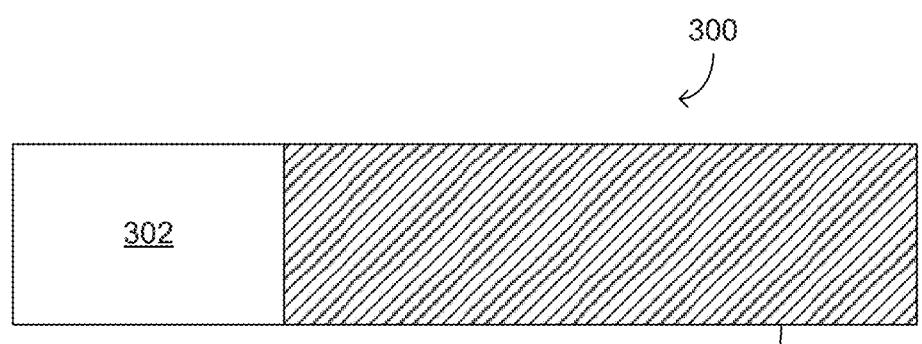
FIG. 3A illustrates an exemplary test strip in an embodiment.
Figure 3B:
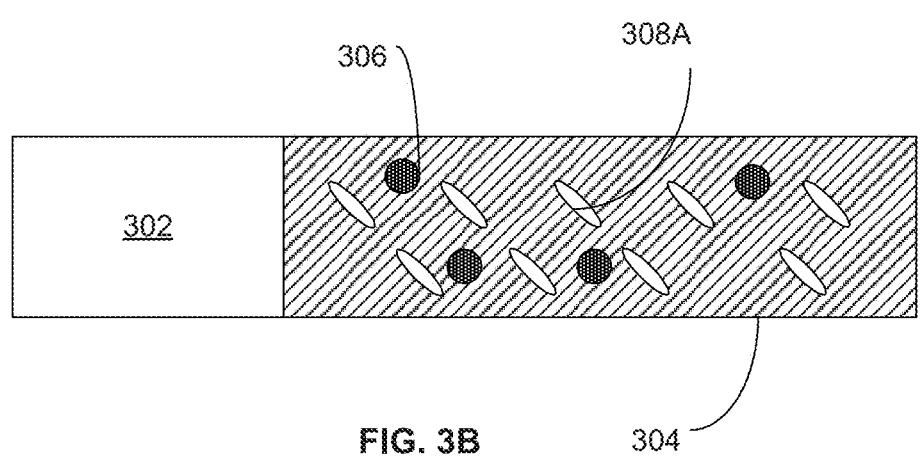
FIG. 3B illustrates an exemplary test strip with water spray containing color reagents in an embodiment.

There are various techniques for visual identification or electrical detection of MIPs exposed to their target molecules. These techniques can use static adsorption, flow absorption or capillary action. FIG. 3A illustrates an exemplary test strip 300 that includes a plastic substrate 302. A portion of the plastic substrate 302 is covered with an MIP film 304. FIG. 3B illustrates that a sample solution 306 can be deposited on MIP film 304 and followed by washing sample solution 306 with a water spray containing a color reagent 308A. When a target molecule hinds to the color reagent, the test strip changes color to indicate a "Yes" for the presence of the target. Otherwise, if no target molecule binds to the color reagent, there is no color change, which indicates "No" for the presence of the target. Color reagent 308A can also provide a range of concentration of the target based upon color intensity.

Figure 3C:
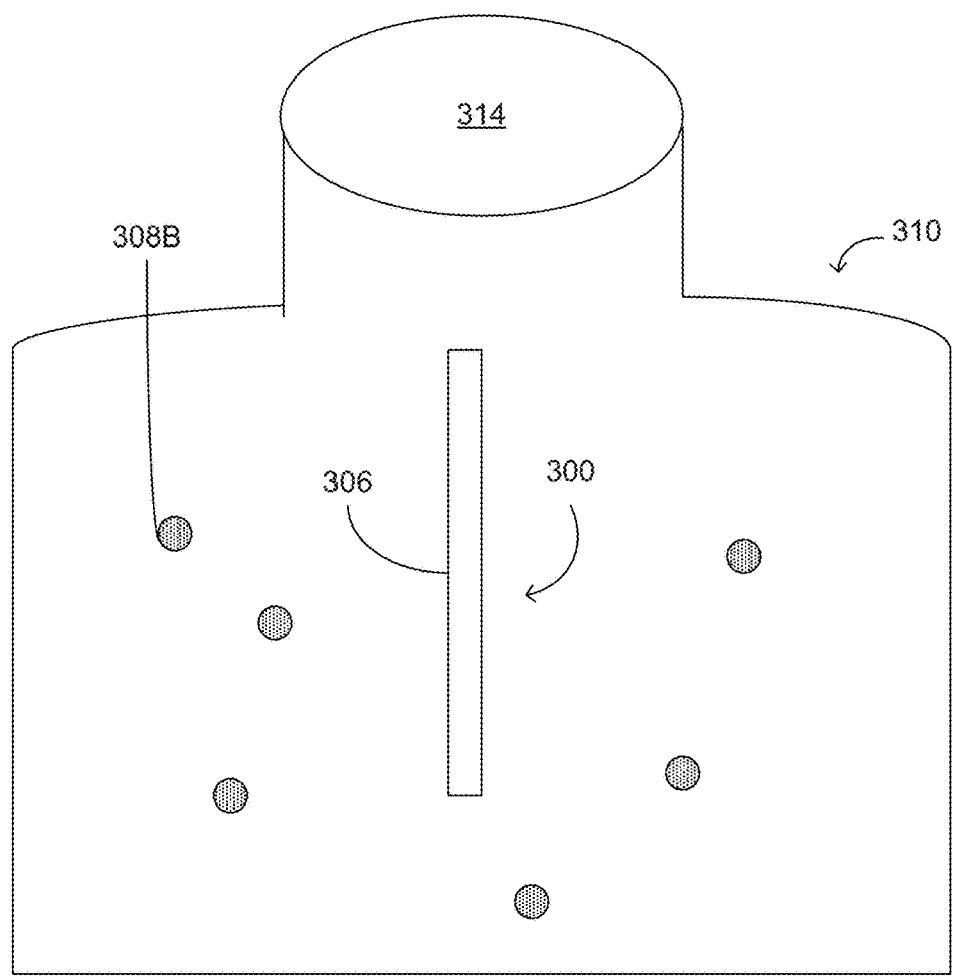
FIG. 3C illustrates an exemplary test strip in a vial with liquid color reagents in an embodiment.

Alternatively, instead of using a water spray containing color reagent 308A, test strip 300 can be used in a vial 310 with a liquid color reagent 308B, as illustrated in FIG. 3C. One can open cap 314 of vial 310, apply sample solution 306 to the MIP film 304, wash off any excess sample, and deposit test strip 300 in vial 310, followed by sealing cap 314 and shaking vial 310 to monitor color change of color reagent 308B.

Figure 3D:
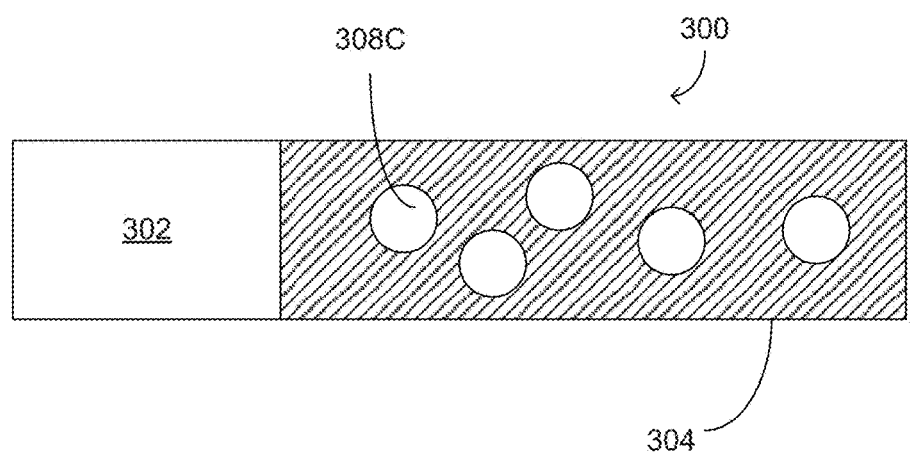
FIG. 3D illustrates an exemplary test strip with color reagents covalently bonded to the MIP film in an embodiment.

FIG. 3D illustrates test strip 300' with color reagent 308C covalently bonded to the MIP film. Color reagent 308C is also capable of covalently bonding with a target molecule. If target sample 306 is present on the MIP film 304, color reagent 308C will change its color to indicate the detection of the target sample.

Figure 4:
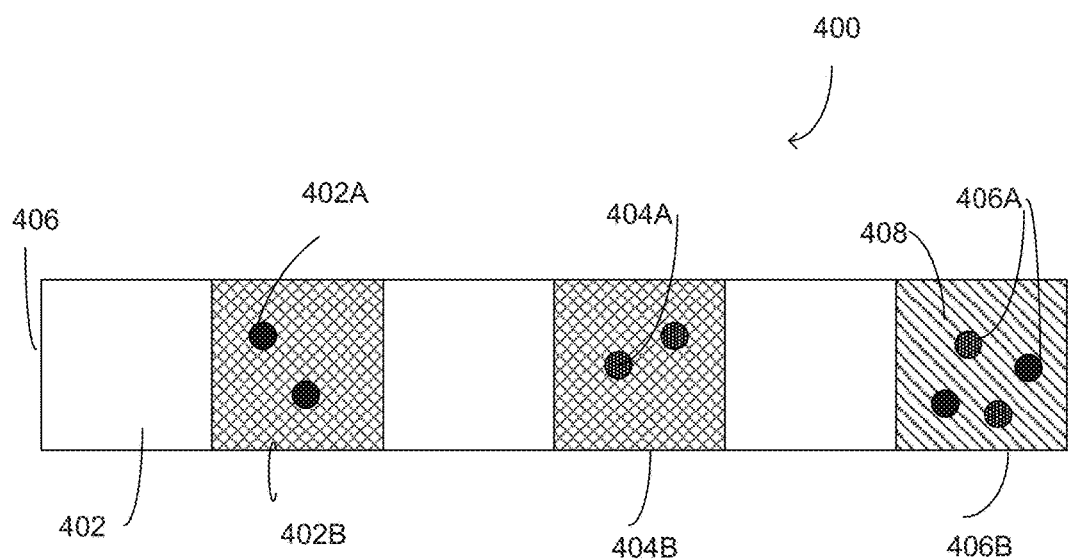
FIG. 4 illustrates an exemplary multi-band test strip in an embodiment.

FIG. 4 illustrates an exemplary multi-band test strip. Multi-band test strip 400 includes a plastic substrate 402 covered with an adsorbing layer 401 (e.g., a paper layer, such as utilized in paper chromatography strips). Multi-band test strip 400 is useful when reagents must be added sequentially. A liquid sample can be added at end 406 to flow through reagent bands 402B and 404B, in the direction of arrow 403. The liquid sample flow picks up reagents 402A and 404A in reagent bands 402B and 404B respectively. A final reagent band 406B includes both a reagent 406A and an MIP film 408. Upon reaching reagent band 406B, if the target is present and has reacted with reagents 402A and 404A, it will react with MIP film 408, and will provide a color change to indicate the presence of the target. Otherwise, no color change occurs.

Figure 5:
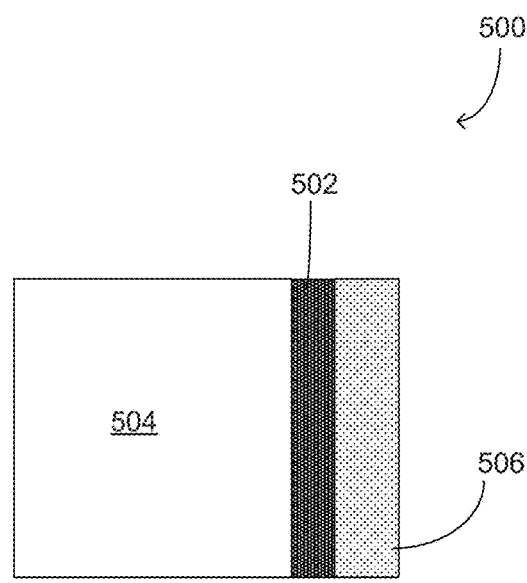
FIG. 5 illustrates an exemplary patch tester in an embodiment.

FIG. 5 illustrates a cross-sectional view of an exemplary sensor for a target molecule. The sensor 500 includes a thin, easily broken membrane 502 that is sandwiched between a reagent reservoir 504 and an MIP film 506. A sample can be applied to the MIP, and excess sample can be washed off. Sensor 500 can be twisted so that the membrane 502 breaks and the reagents from reservoir 504 flow into the MIP film 506 and react with the target to provide color to indicate the presence of the target in the sample. Otherwise, when there is no color, sensor 500 indicates that the sample does not contain the target.

All of these diagnostic methods can be "Yes" or "No" tests for the presence of the target or one can use visual comparisons of the color intensity or a small meter to quantitatively measure the concentration of the target.

Figure 6:
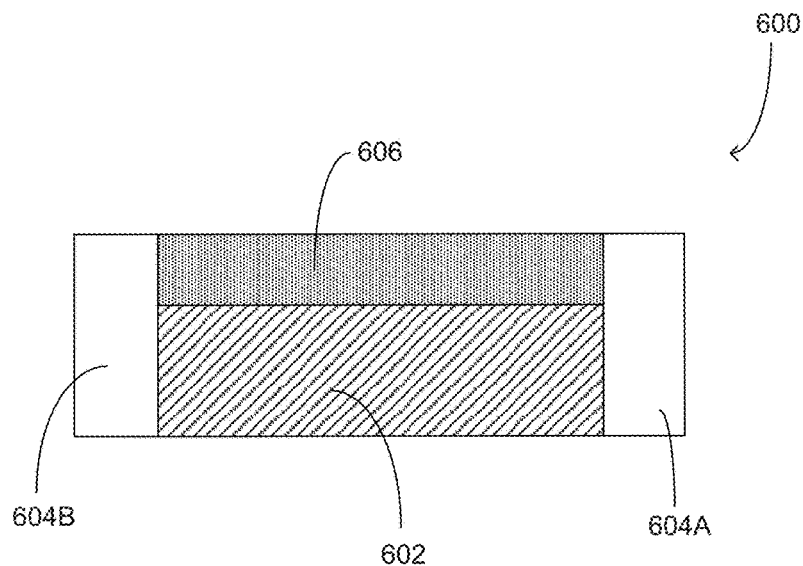
FIG. 6 illustrates an exemplary conductive sensor including an MIP film in an embodiment.

FIG. 6 illustrates a conductive sensor. The sensor 600 includes two electrodes 604A and 604B with an MIP film 606 between the electrodes. The MIP film 606 is supported by a substrate 602 between the electrodes. The substrate 602 is an insulator, for example, a plastic or a glass. There are many other possible configurations for the conductive sensor.

The MIP film can be deposited between the electrodes 604A-604B. A small electric current flows through the MIP film 606, so that the resistance of the MIP film 606 can be measured. The MIP film 606 must be conductive. For example, the MIP film 606 can include a conductive polymer, such as polyaniline. In an embodiment, the MIP film can also be formed from MIP-coated carbon nanotubes (CNTs) and/or single wall carbon nanotubes (SWNTs). The terms CNT and SWNT as used herein are generally interchangeable with SWNTs being a kind of CNT. The MIP-coated CNTs can be used when it is difficult to find a conductive polymer host for a particular target. The MIP-coated CNTs can also be used when it is desirable to have more uniformly sized MIP powders for follow-up analysis by techniques such as HPLC.

MIP films disclosed herein are useful as personal sensors for detecting exposure to harmful target molecules. The sensors that can be worn by a user in contact with an atmosphere that could be contaminated by target molecules.

Figure 7:
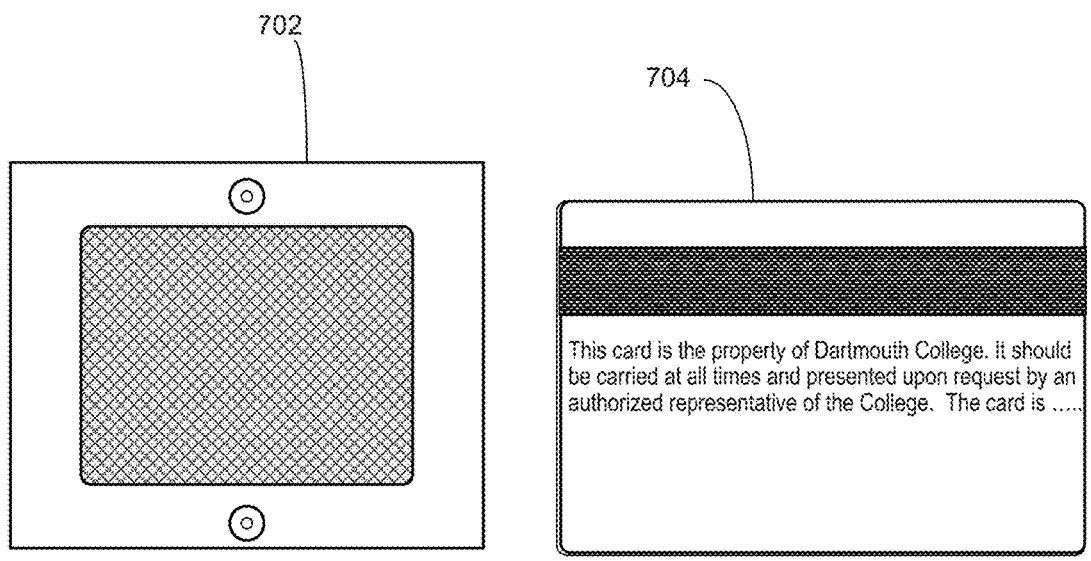
FIG. 7 illustrates a prototype sensor in an embodiment.

In an embodiment, a MIP film personal sensor, a MIP film, and a MIP film sensor may employ radio frequency identification (RFID) technology to report values for exposure to the target molecule in real time. A prototype sensor is shown in FIG. 7. A student identification card 704 is on the right side of sensor 702 as a size reference. The sensor 702 is a clip-on device that is about two inches by two inches by 0.25 inches. For the MIP sensing elements, the MIP film thickness can be about 0.25 inches. This is a small, easily worn device of the same approximate dimensions as, for example, a radiation badge. It is feasible, using for example, ink jet printing, to create a single sensor that has MIPs targeted to a range of organic molecules and to simultaneously monitor all of these sensors that are still in a small package by multiplexing an RFID system, which reports on the exposure level of a selected target in real time.

One of the benefits of the methods disclosed herein over conventional methods for detection of the airborne contaminants is molecular specificity. Because of the extraction of a single contaminant, a post-analysis does not require a separation of the target from other airborne contaminants, which will save time in follow-up analysis. With the uniformly sized MIP powders, the follow-up analysis using HPLC or other techniques is also simpler.

The sensor is passive, because the airborne contaminants are adsorbed by the MIP film by exposure. There is no need for the use of a pump or other moving parts for actively drawing air into the device.

Furthermore, the sensor of the present disclosure fulfils an unmet need, as there currently exists no sensor for the detection of certain airborne contaminants. For example, the sensor as disclosed can also used for detection of cVMS, for which there are no sensors currently available.

Moreover, the device can provide real-time indications of exposure levels. The device is small enough for a user to wear. It can also be desirable to create larger versions of the sensors that can be used to monitor a worksite, a full room or a rental space such as a hotel room or an automobile repair shop, among others. It will be appreciated by those skilled in the art that configuration, shape, and dimensions of the sensor can vary for particular applications.

Formaldehyde Sensor

In an embodiment of the MIP film sensors disclosed herein, the physical property associated with the target molecule's presence in the MIP films is the change in the resistance of the sensing device. Reaction of the target molecule in a PANi/PEI MIP sensor, for example, with a proton from PANi reduces the conductivity of the polymer and yields the detected signal as a change in resistivity (R). While PEI is also protonated by the formic acid solvent in the preparation stage, PEI is not conductive and is present to provide the porosity of the film.

In an embodiment, MIP sensors disclosed herein can be used to measure the presence of airborne formaldehyde and are made with PANi/PEI polymers using formic acid as both a solvent and as a homolog to formaldehyde. Without being bound by theory, a polymerization-initiating step is a feasible mechanism for adsorption of the target molecule, e.g. formaldehyde, given the pKa of formaldehyde and the chemical nature of PANi. Formaldehyde is protonated upon reaching the surface, and that protonation of monomeric formaldehyde is a catalytic step in the formation of polymeric formaldehyde. In an embodiment, both components of a composite film such as PANi/PEI are protonated during production of the casting solution. In an embodiment, such as a MIP with formaldehyde as the target molecule, a single proton abstraction event with subsequent polymerization results in the sequestering of at least two additional unprotonated formaldehyde molecules leading to the formation of trioxane, the simplest polymeric form of formaldehyde. This proposed mechanism implies that particular embodiments of a MIP film may adsorb significantly more formaldehyde than is detected.

Figure 9:
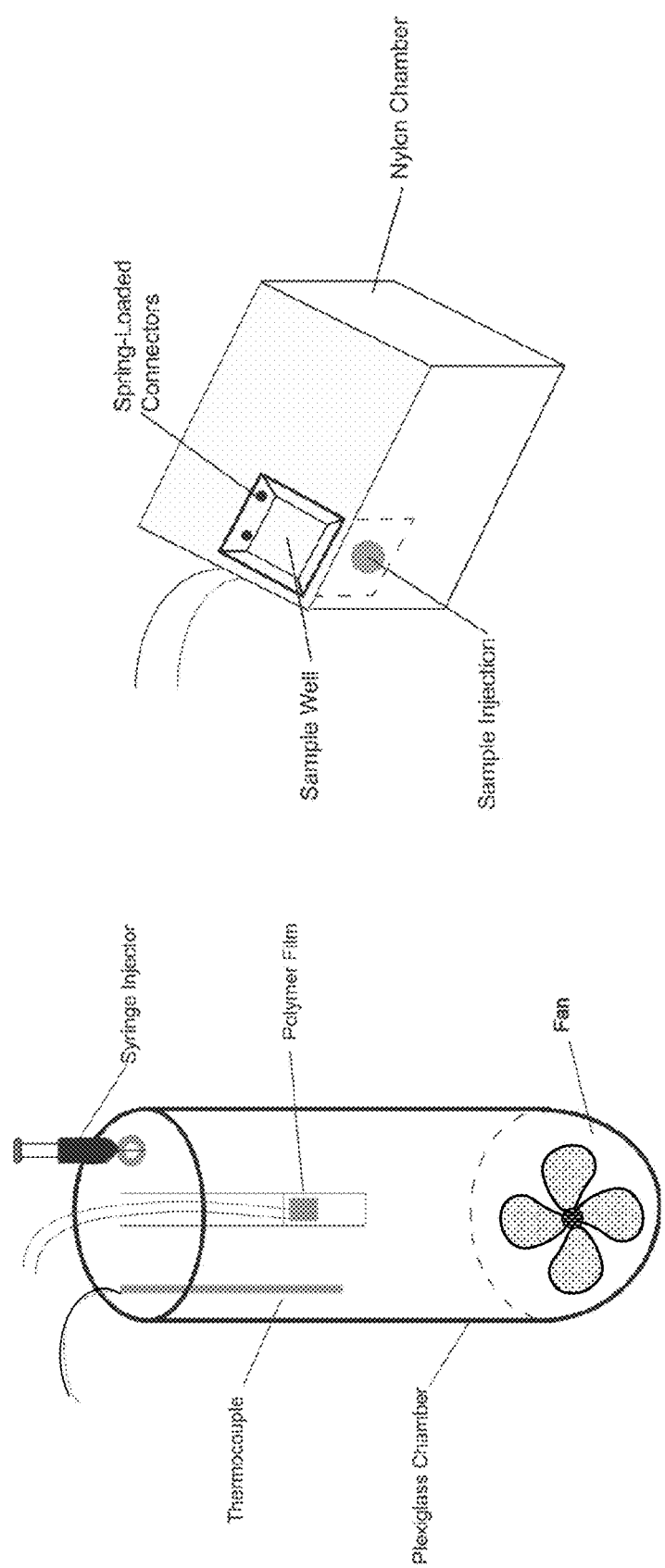
FIG. 9. Schematic drawings of the vapor calibration chamber (left) and the static test chamber (right)

In an embodiment, MIP sensors for formaldehyde were tested in both a static chamber and a vapor phase chamber, see FIG. 9. Injection of formalin (37% formaldehyde) into the sample chamber elicited an immediate rise in the measured resistance. Formalin was injected into the test chambers at different initial temperatures, providing different vapor pressures and different vapor phase concentrations of formaldehyde in air. The resistances of the MIP film sensors having formaldehyde as a target molecule were recorded. The measured resistance of the MIP film sensor was indicative of a response of the MIP film to formaldehyde and provides a measure of the film sensitivity to a quantity of formaldehyde in the airborne sample. Thus, in an embodiment, the MIP film sensors presented herein can detect airborne target molecules.

Figure 10:
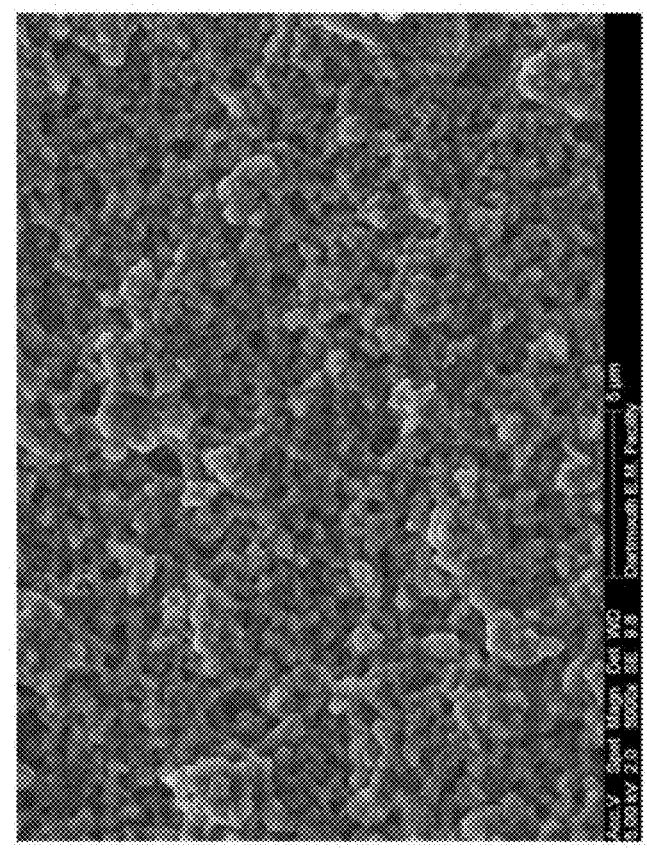
FIG. 10. SEM images of 5% PANi (left) and 5% PANi/5% PEI films (right).
Figure 10:
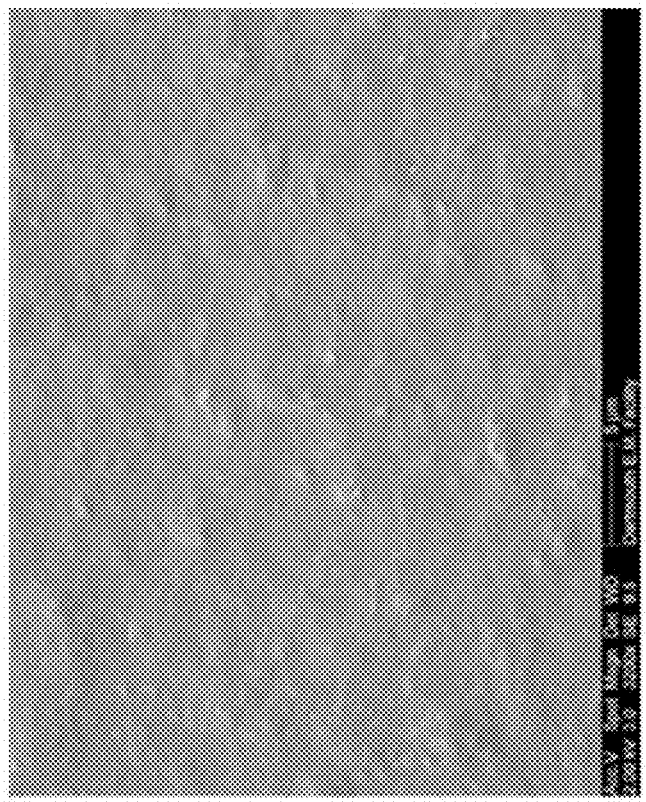

The morphology of the film surface of MIP sensors produced by methods disclosed herein was further investigated by scanning electron microscopy (SEM) of MIP films produced on glass or oxidized silicon under the coating conditions described above. FIG. 10 depicts SEM images of a 5 weight percent PANi film and also a 5 weight percent PANi/5 weight percent PEI composite film. As depicted in FIG. 10, the pure PANi film is very smooth, while the composite PANi/PEI film shows highly developed porosity and offers significantly better responsivity to the target molecule. Thus, in an embodiment, the porous composite film provides a material for adsorption of the target molecule, e.g. formaldehyde, in the vapor/gas phase.

Figure 11:
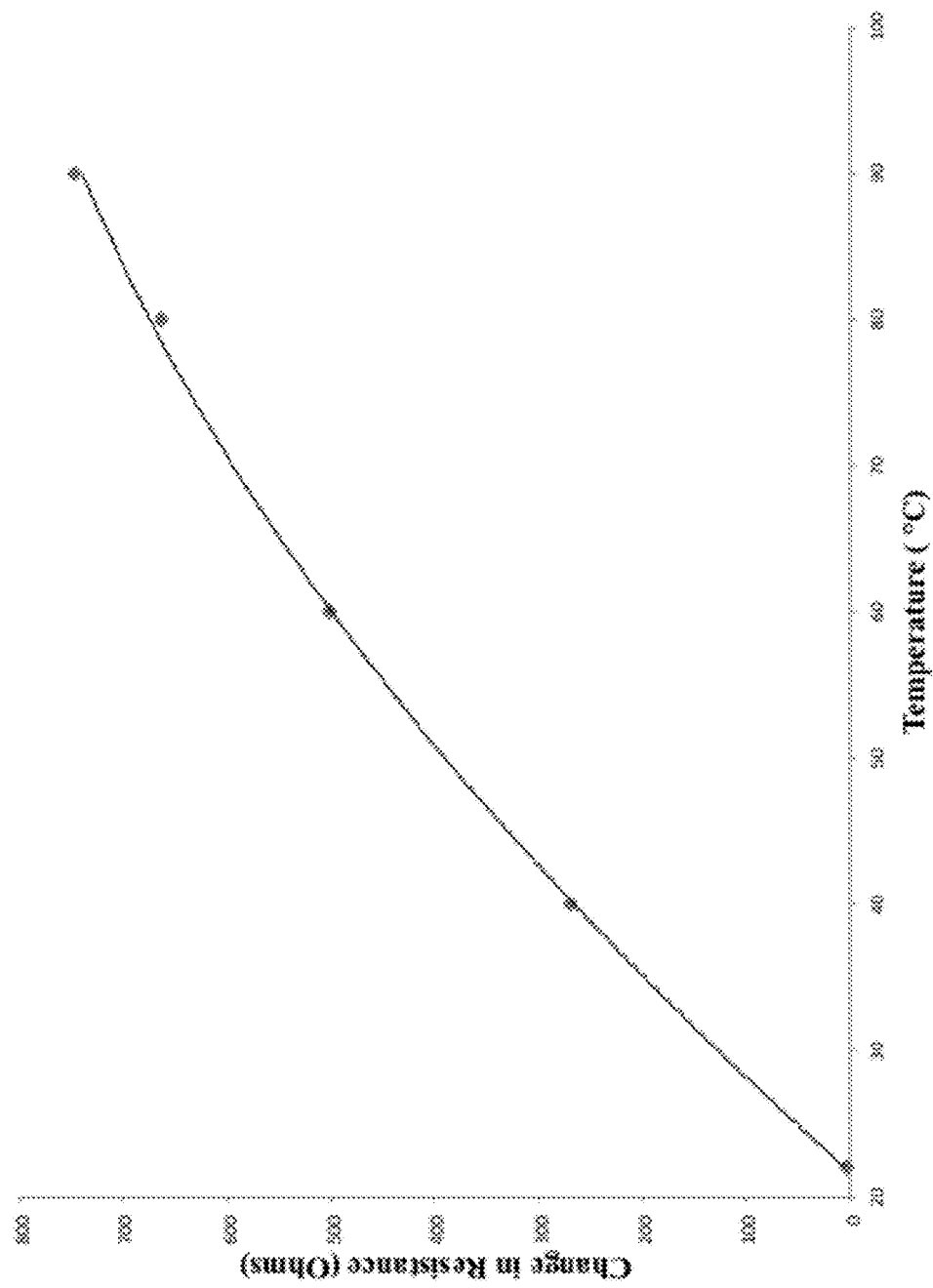
FIG. 11. Relative resistance as a function of temperature for exposure of the polymer film to formaldehyde in the static chamber.

FIG. 11 demonstrates the responsiveness of an embodiment of a PANi/PEI MIP film to formaldehyde when formaldehyde is the target molecule. The static chamber results for injections of formaldehyde over five different nominal temperatures over the range from 22° C. to 90° C. with a 5 s exposure are depicted in FIG. 11. The sample begins to cool almost immediately upon injection causing a deviation of the fit from an exact correlation with temperature. In addition, there is an inherent, background, resistance for all of the sensor devices. The trend of increasing resistance with increasing temperature is depicted in FIG. 11 and demonstrates the responsiveness of an embodiment of a MIP film to formaldehyde.

The vapor phase chamber of FIG. 9 was used to obtain a calibration of an embodiment of a MIP film sensor device having formaldehyde as the target molecule with respect to the amount of formaldehyde present in air. The complete vaporization of the injected sample in the test chamber provides data for calibration of the MIP sensor as follows. The gas phase concentration in air sample is calculated assuming ideal gas behavior at a known temperature and our measurements were made at 25° C. Samples as small as 1 µL were injected, providing a minimum concentration of vapor phase formaldehyde of 40 ppm in air. In an embodiment, this minimum sample size was not limited by the MIP film response, but by the testing apparatus used.

Figure 12:
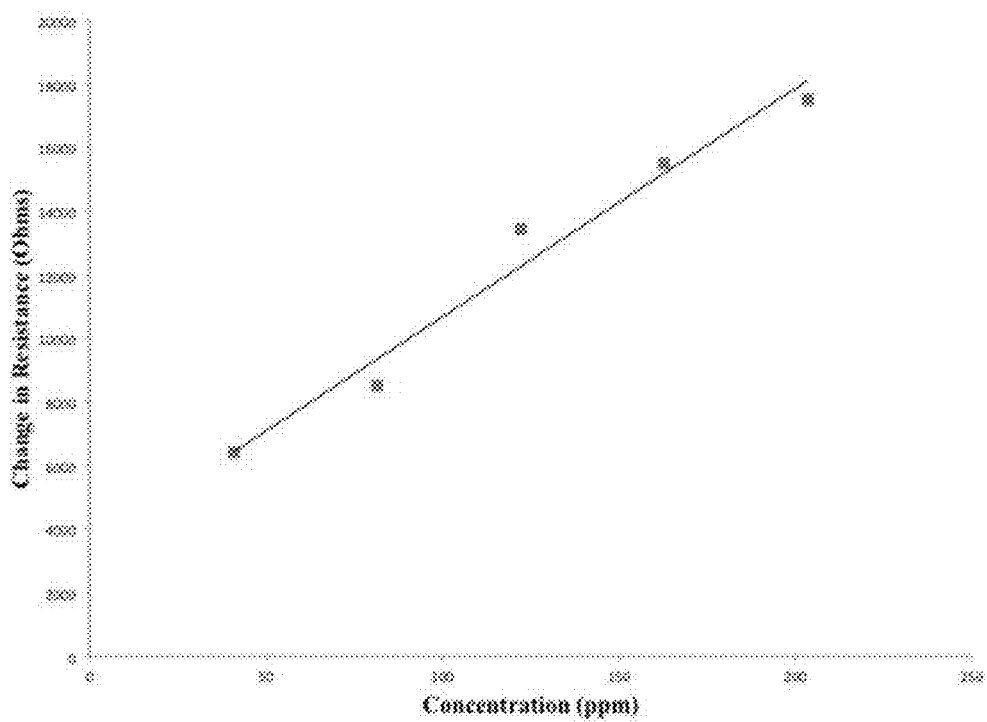
FIG. 12. Plot of film response as a function of concentration (upper) and the time response of exposure of the film to a vaporized sample formalin or approximately 170 ppm of formaldehyde lower).
Figure 12:
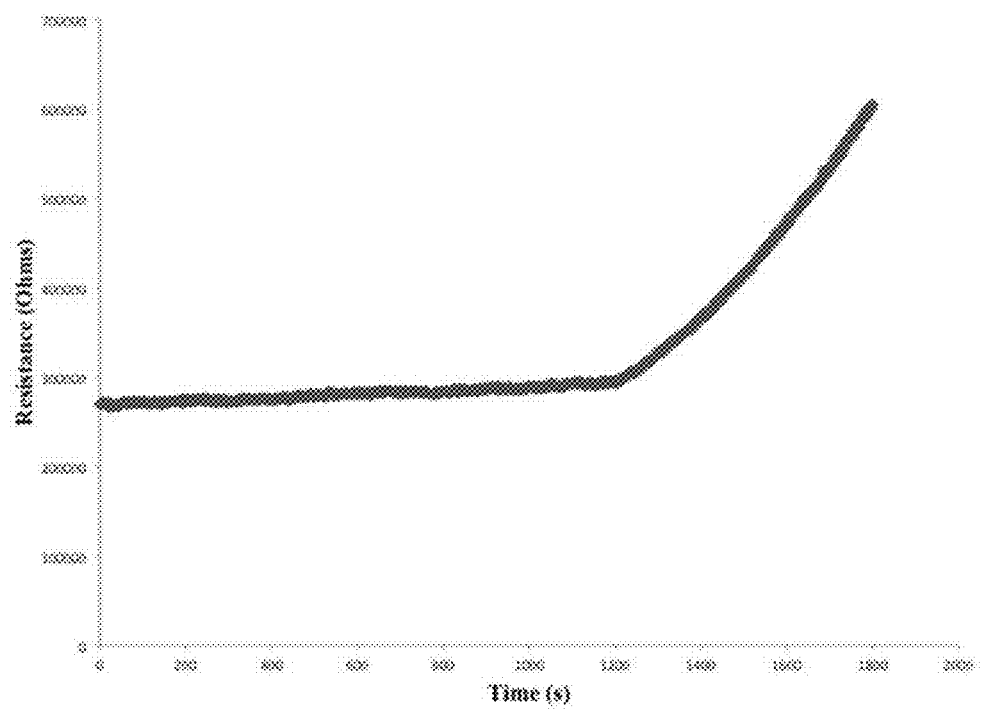

In one embodiment, a MIP sensor device was calibrated by recording the resistance after a constant delay, post-injection. In the case of the data presented in FIG. 12, this time delay was one minute. Also depicted in FIG. 12 is a plot of the real-time data for injection of a 5 µL sample of formalin. As further depicted in FIG. 12, the resistance continues to rise over the ten minute post-injection timeframe. Thus, in embodiments of the MIP film, it will continue to adsorb the target molecule as long sample remains in the nascent atmosphere and surface sites in the MIP film are available. Longer measurement times generally will provide greater signal changes.

Figure 13:
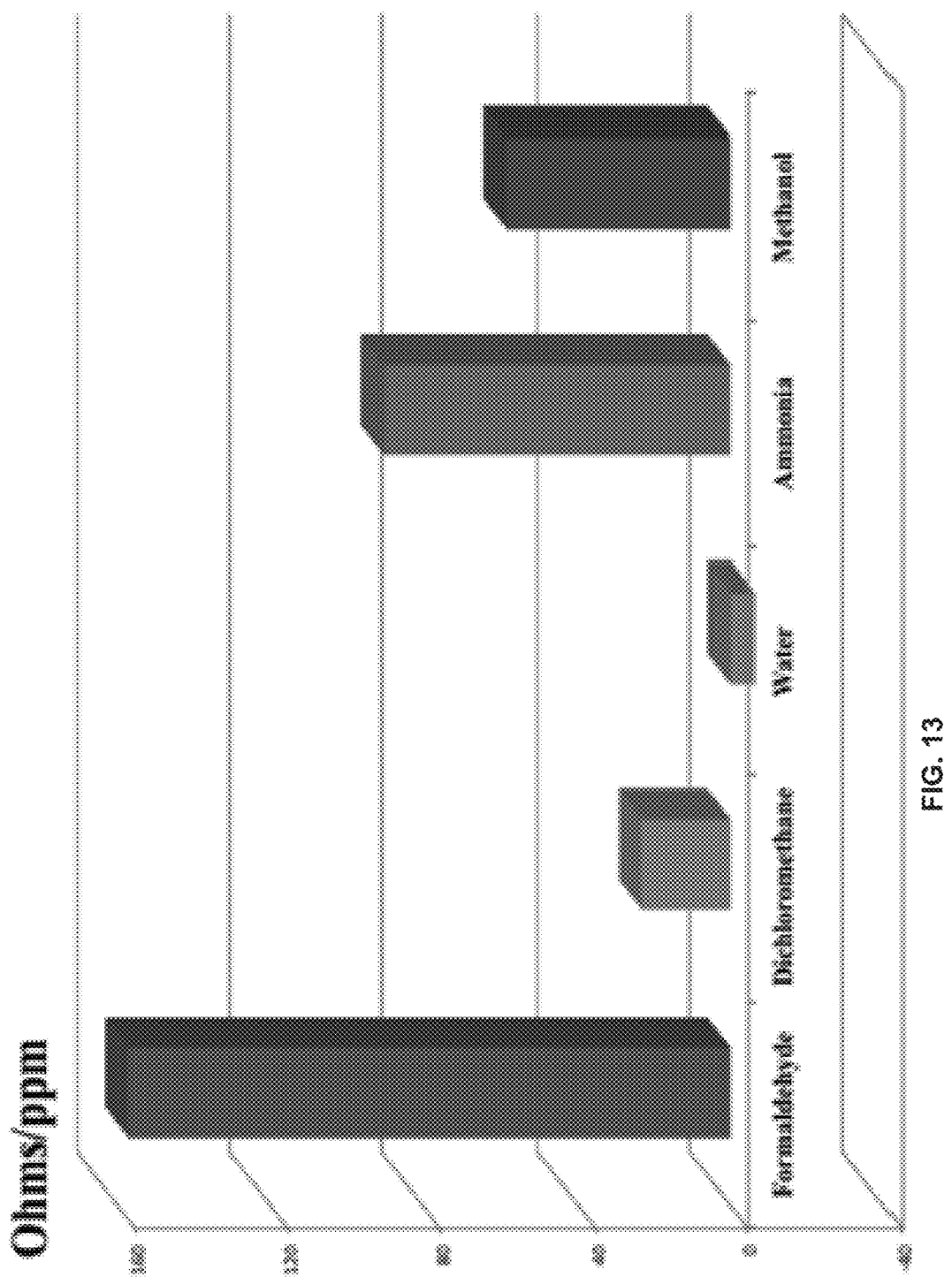
FIG. 13. Relative resistance as a function of exposure of the polymer film to 100% samples of formaldehyde, water and other volatile organic molecules.

While sensitivity is a crucial component of any sensor, a sensor should also be specific or, at the least more sensitive to, the desired target than any interfering molecules. In one embodiment, a MIP film designed to detect formaldehyde was tested with four other molecules, and the results are depicted in FIG. 13. FIG. 13 depicts that formaldehyde is selectively adsorbed by a MIP film sensor that has formaldehyde as a target molecule. FIG. 13 depicts that the most significant potential interferent is ammonia. Ammonia is a base and is expected to have significant reactivity with the acidic proton on PANi and thus the PANi/PEI MIP film sensor exhibited some non-specific reactivity with ammonia. As depicted in FIG. 13, the response to methanol is approximately one-fourth that of the target formaldehyde. The response for water indicates that it does not significantly affect the MIP film operation. This observation is supported by the use of formalin as the source of formaldehyde in embodiments of the MIP film sensor for formaldehyde discussed above where formalin, in which solutions commonly contain from about 37% to 50% or greater water by weight, were injected and tested as a formaldehyde source.

Carbon Nanotube MIP Sensor

In a non-limiting embodiment, carbon nanotube sensors coated with a MIP are used to measure and/or detect target molecules. Resistivity measurements of embodiments of sensors with MIP coated carbon nanotubes with and without target molecules bound demonstrate the detection of target molecules by these MIP coated carbon nanotube sensors. Embodiments of the MIP coated carbon nanotube sensors were also tested with molecules related to the target molecule to test the specificity of the MIP coated carbon nanotube sensors.

Figure 8:
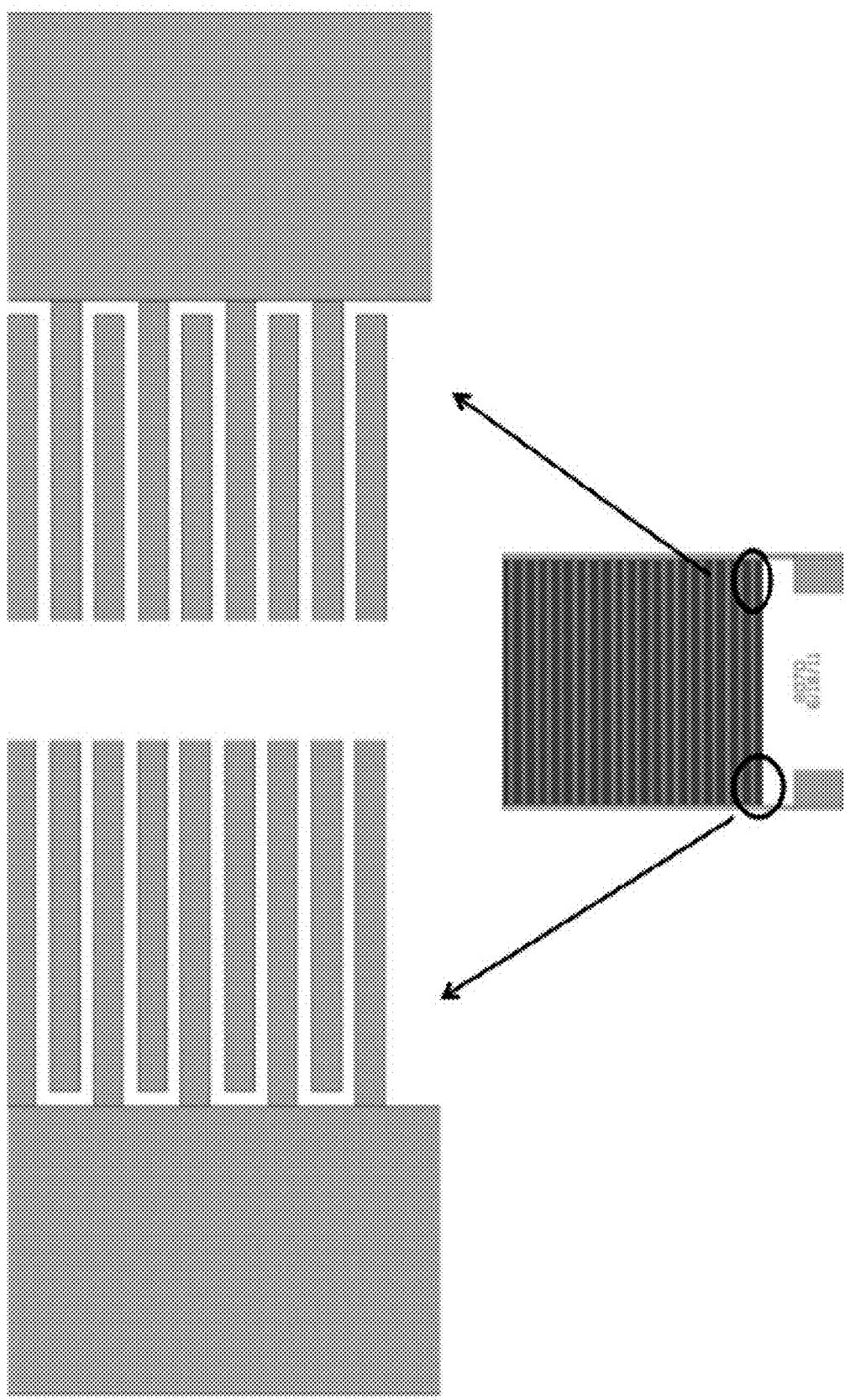
FIG. 8. Schematic diagram of the lithographic circuit for a sensor with interdigitated electrodes: of 40 μm and a spacing of 20 μm.

In an embodiment, MIP coated carbon nanotube films can be cast or otherwise coated upon surfaces to create target molecule specific sensors. In general, a target molecule can be dissolved in a first solvent along with a host polymer that is non-conductive to make a structural component only MIP solution. The structural component only MIP solution can then be mixed with a solution containing carbon nanotubes. The MIP and carbon nanotube solution can then be cast upon a surface, such as an electrode, forming a MIP coated carbon nanotube film on a surface. FIG. 8 depicts an embodiment of a sensor, in the form of an electrode, upon which MIP coated carbon nanotube films can be coated.

In a particular embodiment, films of MIP coated SWNTs using PVPy as the polymer (with cotinine as a target molecule) and control (polymer only with no target molecule) coated SWNTs were deposited on the electrodes depicted in FIG. 8 and the resistance of these devices was measured. The resistance of the MIP film with cotinine was 2.05 kΩ (similar to the resistance of the bare carbon nanotubes), and that of the unimprinted control film without cotinine was 7.18 kΩ, a 250% difference. After extraction with toluene of the cotinine from the MIP film, the resistance increased to 6.41 kΩ while the control film resistance was unchanged after the same procedure.

In an embodiment, the MIP coated carbon nanotube film may be regenerated by extracting the target molecule and then exposing the MIP coated carbon nanotube film to a particular gas or liquid sample to detect and/or measure for a target molecule. In one embodiment, reinsertion of cotinine into the MIP film decreased the resistance from about 7 kΩ to nearly the original value of 2.87 kΩ.

In an embodiment, the regenerative qualities of the MIP coated carbon nanotube films were demonstrated through recycling the films through subsequent rounds of extraction and reinsertion of the target molecule. In an embodiment, the target molecule was cotinine and the electrodes depicted in FIG. 8 were coated with MIP coated carbon nanotubes and control coated carbon nanotubes. The MIP film resistance measured 2.25 kΩ, and the control film, 7.34 kΩ, a 262% difference. In a first regeneration, extraction of the cotinine raised the MIP film resistance to 7.50 kΩ and reinsertion of the cotinine lowered the resistance to nearly the original value, 2.70 kΩ. In a second regeneration, the MIP sensor exhibited a resistance of 3.69 kΩ while the control film resistance was 11.75 kΩ, a 218% difference. In a third regeneration, the MIP sensor resistance increased to 11.11 kΩ, and after cotinine reinsertion, the MIP sensor resistance decreased to 4.38 kΩ.

Thus, in an embodiment, conductive films made by spin coating molecularly imprinted PVPy onto SWNTs have significantly different conductivity than SWNTs coated with pure PVPy, that is unimprinted films. Furthermore, in a particular embodiment, when cotinine is extracted from the MIP film, it has a conductivity value similar to that of the control film, and when cotinine is reinserted into the MIP film, the film returns a conductivity value similar to that measured prior to cotinine extraction in toluene. Thus, in an embodiment, the MIP coated carbon nanotube films can be reused through subsequent rounds of regeneration.

Non-specific changes in resistivity of the sensors described above were tested through making attempts to insert cotinine into control films by following the identical procedure employed for the MIP sensors presented above. This test was to ensure that cotinine reinserted into the MIP sensors was not adhering onto the glass or the surface of the polymer and thus non-specifically changing the resistivity. A small decrease in measured resistance of cotinine exposed control carbon nanotube sensors was observed. This change in resistance is attributed to non-specific binding. However, the magnitude of the change is indicative of a very small amount of target molecule indiscriminately adsorbing to the polymer surface in the control or sensor devices.

Using the methods disclosed herein, the MIP sensors are generally more sensitive to the target molecule than any other potential interfering molecule. In an embodiment, a cotinine target molecule MIP coated carbon nanotube sensor film was tested against nicotine, structurally similar to cotinine, but lacking the carboxyl group on the pyrrolidine ring. The cotinine target molecule MIP coated carbon nanotube sensor had a resistance of 4.18 kΩ Extraction of the cotinine increased the resistance to 7.31 kΩ and attempts to insert nicotine into the sensor decreased the resistance only slightly, on the same order as the non-specific binding discussed above, to 6.57 kΩ, demonstrating the specificity of the cotinine target molecule MIP coated carbon nanotube sensor for cotinine detection.

The regenerative capacity of the sensors for rebinding target molecule can be quantified by gas chromatography. In an embodiment, blank glass slides, control films and imprinted films were subjected to the extraction and reinsertion processes described above, for cotinine and the quantity of cotinine was determined. The results are shown in Table 1. The cotinine target molecule MIP coated carbon nanotube film had a significantly higher cotinine concentration than either the blank or control films. Almost three times as much cotinine was reinserted into the MIP film as into the control film. Thus, in an embodiment, the change in conductivity of an MIP film demonstrated that the imprinted polymer was selectively adsorbing the target molecule.

TABLE 1

GC data for insertion of cotinine into extracted films.

| Sample | cotinine ng/mL | ng cotinine |
|---|---|---|
| Blank | 750 | 3000 |
| Control | 1050 | 4200 |
| MIP | 3000 | 12000 |

The IR spectra of MIP and related films, unsupported by the carbon nanotubes, provided a baseline for comparison of the embodiments of the sensors presented herein. IR spectra of cotinine films revealed a carbonyl absorption band at 1675 $cm^{-1}$; PVPy films exhibited a carbonyl band at 1652 $cm^{-1}$. The carbonyl band of the cotinine-imprinted PVPy film was observed at 1658 $cm^{-1}$ with a significant increase in intensity, indicating an interaction between the host polymer and the template.

IR spectra of the MIP-SWNT films showed that the carbonyl bands of both components were significantly shifted to higher energy. The control SWNT-supported PVPy band occurred at 1767 cm-1 and the cotinine-imprinted MIP-SWNT band at 1769 cm-1, with a significant increase in intensity compared with the control. This observation is consistent with the interaction reported for a PVPy-C60 complex. The IR spectra were used as an indicator of imprinting, template extraction and molecule insertion.

In an embodiment, based on the shift in the carboxyl adsorption peak in the infrared spectrum of cotinine in isolated and imprinted situations, both hydrogen bonding and shape recognition occurred in the MIP films. Thus, the carbonyl group on cotinine is likely interacting with the hydrogen in the β-position, with respect to the carbonyl group in the PVPy polymer, to add a chemical component of the interaction to the shape-recognition sites in the MIP.

EXAMPLES

Preparation of PANi/PEI Composite Solutions

Poly(aniline) was purchased from Polysciences, Inc. as the undoped, emeraldine base form with a molecular weight of 15,000 and a conductivity of 10e-10 S/cm. Branched poly(ethyleneimine), PEI, with a molecular weight 70,000 g/mol was obtained from Alfa-Aesar as a 30% aqueous solution. Formic acid, >98%, was purchased from EMD Chemicals and used to dissolve the polymers prior to spin casting. Formaldehyde was purchased from Fisher Scientific as formalin solution (37% formaldehyde) containing both water and a small quantity of methanol. All reagents were used as received without any further treatment.

The polymer films for detecting formaldehyde were spin-cast composites of PANi and PEI. PANi in its conductive form is insoluble. However, the emeraldine base may be dissolved in several solvents, including the formic acid used in this research. PEI is also soluble in formic acid and the formic acid solvent also acts as the dopant for PANi. The spin casting solution was produced as a 5% (by weight) solution in each of the two polymers. As a result of the inclusion of doped-PANi, protonated solutions are green, while solutions of the unprotonated material are deep blue.

Construction of Conductive Devices

The conductive sensors were constructed on oxidized silicon substrates with the PANi/PEI composite film as the active element above the electrode. The production method is briefly outlined below and the results depicted in FIG. 8.

Prime grade silicon wafers with a 5000 Å thermally deposited oxide layer were used for the substrate. These films were patterned by photolithography and subsequently wet etched to produce the final electrodes with a total area of 376 $mm^2$, following vapor deposition of 1000 Å of chromium and the 200 Å overlayer of nickel. Lift off was accomplished using acetone, with final rinses of water. The electrode was patterned into an interdigitated grid, as shown in FIG. 8, with 40 ium fingers and 20 pm spacing.

Next, the PANi/PEI polymer layer was spin-coated onto the electrode. An aliquot of 1 mL of solution was dropped onto the electrodes, and allowed to spread for 20 seconds. The spin-coater was then brought up to 1800 rpm for 30 seconds. This resulted in the deposition of films with a typical thickness of 300 nm. After this treatment, background resistance values are measured, and the sensor is ready for use in binding studies. Morphology of the thin films was investigated by scanning electron microscopy using a FEI Company, XL-30 ESEM-FEG field emission gun environmental scanning electron micro scope.

Measurement Chambers

Two different test chambers were used. Schematic diagrams of the two systems are depicted in FIG. 9 and described below. The static chamber, depicted on the right side of FIG. 9 uses the vapor pressure of the molecule over the liquid as the source of the gaseous sample, while the vapor chamber, depicted on the left side of FIG. 9, relies on evaporation of the complete sample in air after injection into the chamber well away from the film. The static sample system consists of a small nylon box, containing spring-mounted electrodes and an approximately 3 $cm^3$ well that is filled via a syringe through a septum. The sensor assembly is placed on the electrodes above the well and a nylon cover is secured using a torque wrench to ensure reproducible pressure of the sensor against the spring-mounted electrodes.

Formaldehyde (1 mL) at a known temperature is injected into the well and the response of the sensor is recorded. To follow the recovery of the sensor after exposure to formaldehyde, dry nitrogen is passed through the well to evaporate the sample. The change in the resistance of the sensor is measured using a multimeter connected to a laboratory computer.

The vapor chamber is a ~8 L cylindrical chamber that is outfitted with a fan at the bottom and a cover that allows for a sensor holder so that the device is located approximately halfway along the 30 cm length. The cover also contains a port through which a microliter syringe may be inserted and a second port that allows mounting of a thermocouple. Electrical contact is made between sample device and the holder, the fan is switched on and a small quantity of formaldehyde (1-5 µL) is injected. Evaporation of the sample is very fast and the film detects the vapor nearly instantly. The chamber is not evacuated prior to use, so that the formaldehyde vapor is diluted with air at atmospheric pressure. The change in resistance is monitored using the same multimeter and computer as for the static chamber.

Sensor Response

The physical property associated with presence of the target molecule in the film is the change in the resistance. Sensor functionality depends upon detecting differences in this property as a function of the adsorption of the target formaldehyde molecule onto the device. Numerous films/devices were tested using formalin both in the small static chamber and in the vapor chamber. The response of the sensing film to potentially interfering molecules was also examined.

The resistance, R, of the polymer film was measured with a Keithley Model 2100 6½ Digit Multimeter. During the measurement, a constant current of 1 mA was applied and the voltage through the film was recorded, providing a resistance value via Ohm's law. Total dissipated power within the film is less than 2 W. Four point measurements were found unnecessary and all of the reported data were obtained using two contacts, an inherently simpler measurement. Data were taken at a rate of 1 Hz over a period of several minutes.

The resistance increased by as much as 6 kΩ from its background value prior to exposure through to a plateau associated with the level of formaldehyde in the static sample chamber. Larger changes in R, greater than 15 kΩ, were observed in the vapor system.

Preparation of MIP-SWNT Suspensions

The MIP-coated nanotubes were prepared by suspending 20 mg of SWNTs (BuckyUSA BU-202, 0.5-10 µm in length, 0.7-2.5 nm in diameter), 10 mg of PVPy (Polysciences, Inc. Cat#:01051 MW: 40,000), and 5 µL of cotinine (Alfa Aesar L11873) in 50 mL of absolute ethanol (Deacon Laboratories, Inc.). A control suspension was produced with the identical mixture minus the cotinine. Both suspensions were sonicated for four hours. After sonication, the suspensions were filtered through a 60 mL funnel containing a fit with 4.5-5 µm pores. The CNTs left on the frit were washed five times with ethanol in order to remove any unbound PVPy or cotinine. The dried, coated CNTs were re-suspended in 20 mL of ethanol by sonication for one hour.

Coated Carbon Nanotube Sensor Production and Measurement

The conductive sensors were constructed on glass substrates using chromium metal for the electrode and the PVPy-SWNT film as the active element above the electrode. The electrode was patterned into an interdigitated grid, as depicted in FIG. 8, with 40 µm fingers and 20 pm spacing. The electrodes were produced by photolithography and the electrode surface encompassed a total area of 376 mm$^2$. The PVPy-SWNT layer was spin-coated onto the interdigitated electrode. An aliquot of 200 µL of the suspension was dropped onto the substrate and allowed to spread for 20 seconds. The spin-coater was then brought up to 2100 rpm for 30 seconds and after coating the samples were baked at 60° C. for 20 minutes. This resulted in the deposition of films with a consistent thickness of approximately 300 nm. After this treatment, background resistance values were measured.

In order to completely extract the cotinine template, the sensors were soaked in 5 mL of toluene for 12 hours. This was followed by a wash with fresh toluene in order to remove any cotinine that still adhered to the glass or the film surface. The films were then dried. The resistance of the films was re-measured to provide the cotinine-extracted value.

Reinsertion of cotinine into the MIP-SWNT films was accomplished by placing the sensor in 5 mL of a 10% solution of cotinine in ethanol. Following this exposure, the films were washed with fresh ethanol to remove surface-adhered cotinine and then allowed to dry. Resistance measurements were then taken for the cotinine-reinserted values.

The resistance of the film was measured using a Fluke 8000A Digital Multimeter. During the measurement, a constant current of 1 mA is applied and the voltage through the film is recorded, providing a resistance value via Ohm's law. Total dissipated power within the film is less than 2 W. Two point measurements were sufficient to signal the presence or absence of the cotinine template molecule in the sensor.

Gas Chromatography and Infrared Spectroscopy Measurements

As a confirmation of the conductivity measurements, quantitative gas chromatography was also performed on the MIP-SWNT suspensions. The MIP-SWNT and control SWNT suspensions were coated onto glass substrates using the procedure described above. The cotinine extraction and reinsertion into these films followed the processes described above. Following the reinsertion, the cotinine reinserted into the film was determined by a second extraction into toluene. One milliliter aliquots of this extraction solution were then analyzed on a HP-5 column following the addition of quinoline as the internal standard and reduction of the volume to approximately 20 µL. Samples were analyzed on a Perkin Elmer Auto System XL Gas Chromatograph equipped with a flame ionization detector in duplicate and compared to a standard curve.

Infrared spectroscopy was used as a test for the presence or absence of the cotinine template in the deposited films. Spectra were obtained using one-inch square substrates and following the procedure detailed above for creating samples.

The attenuated total reflection infrared spectrum of the prepared samples was recorded. Spectra were also obtained of films produced using an MIP-SWNT suspension from which the cotinine had been extracted through the following steps: 10 ml, of MIP-SWNT suspension were filtered; the nanotubes were re-suspended in 10 mL of toluene, noting that cotinine is soluble in toluene and PVPy is not; the solution was stirred for 30 min; the nanotubes were filtered and washed five times with toluene; and re-suspended in 10 mL of absolute ethanol. Spectra of cotinine-reinserted films were then obtained using the cotinine-extracted MIP-SWNTs that were re-suspended in 10 mL of a 5% cotinine in ethanol solution.

Having described several embodiments, it will be recognized by those skilled in the art that various modifications, alternative constructions, and equivalents can be used without departing from the spirit of the disclosure. Accordingly, the above description should not be taken as limiting the scope of the disclosure.

Those skilled in the art will appreciate that the presently disclosed instrumentalities teach by way of example and not by limitation. Therefore, the matter contained in the above description or shown in the accompanying drawings should be interpreted as illustrative and not in a limiting sense. The following claims are intended to cover all generic and specific features described herein.

What is claimed is:

1. A molecularly imprinted polymer sensor for sensing a target molecule, comprising:
    a porous polymer film molecularly imprinted with the target molecule and including:
        (a) a conductive polymer having resistance sensitive to binding with the target molecule, and
        (b) intermixed with the conductive polymer, a structural polymer different from the conductive polymer and providing porosity to the porous polymer film; and
    interdigitated electrodes, located on a surface of the porous polymer film, for measuring a change in the resistance to sense said binding.

2. The molecularly imprinted polymer sensor of claim 1, wherein the structural polymer is non-conductive.

3. The molecularly imprinted polymer sensor of claim 1, wherein the target molecule is an airborne target molecule.

4. The molecularly imprinted polymer sensor of claim 1, wherein the conductive polymer and the structural polymer are mixed throughout the porous polymer film.

5. The molecularly imprinted polymer sensor of claim 4, wherein a molar ratio of the conductive polymer to the structural polymer is between 10:1 and 1:10.

6. The molecularly imprinted polymer sensor of claim 1, wherein the structural polymer includes polyethyleneimine.

7. The molecularly imprinted polymer sensor of claim 1, wherein the structural polymer includes nylon.

8. The molecularly imprinted polymer sensor of claim 1, wherein the structural polymer includes nylon-6.

9. The molecularly imprinted polymer sensor of claim 1, wherein the conductive polymer includes polyaniline.

10. The molecularly imprinted polymer sensor of claim 1, wherein the porous polymer film has thickness between 50 and 500 nanometers.

11. The molecularly imprinted polymer sensor of claim 10, wherein the interdigitated electrodes has finger spacing in range between 10 and 30microns.

12. The molecularly imprinted polymer sensor of claim 1, the structural polymer providing the porosity to the porous polymer film in regions where the structural polymer and the conductive polymer are intermixed.

* * * * *